(12) United States Patent
Pasricha et al.

(10) Patent No.: US 7,659,306 B2
(45) Date of Patent: Feb. 9, 2010

(54) METHOD OF INCREASING GASTRIC EMPTYING

(75) Inventors: Pankaj Jay Pasricha, Houston, TX (US); Maria-Adelaide Micci, League City, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 318 days.

(21) Appl. No.: 11/266,686

(22) Filed: Nov. 3, 2005

(65) Prior Publication Data

US 2006/0116350 A1 Jun. 1, 2006

Related U.S. Application Data

(60) Provisional application No. 60/624,603, filed on Nov. 3, 2004.

(51) Int. Cl.
*A61K 31/40* (2006.01)
(52) U.S. Cl. .................................................... 514/428
(58) Field of Classification Search .................. None
See application file for complete search history.

(56) References Cited

OTHER PUBLICATIONS

The Merck Manual, 17$^{th}$ edition (1999), pp. 221-223.*
U.S. Food and Drug Administration Letter issued Jan. 24, 2000 for Propulsid.*

* cited by examiner

*Primary Examiner*—Phyllis G. Spivack
(74) *Attorney, Agent, or Firm*—Benjamin Aaron Adler

(57) ABSTRACT

The invention discloses the administration of nafadotride partially reverse the effect of dopamine on gastric emptying in patients suffering from gastroesophageal reflux.

4 Claims, 3 Drawing Sheets

METHOD OF INCREASING GASTRIC EMPTYING

CROSS-REFERENCE TO RELATED APPLICATION

This non-provisional application claims benefit of provisional U.S. Ser. No. 60/624,603, filed Nov. 3, 2004, now abandoned.

BACKGROUND OF THE INVENTION

1. Field of the Invention

The present invention relates generally to the fields of gastric functions and dopamine receptor research. More specifically, the present invention relates to uses of dopamine 3 receptor agonists and antagonists in the treatment of gastrointestinal disorders.

2. Description of the Related Art

Gastrointestinal (GI) motility regulates the orderly movement of ingested material through the gut to ensure adequate absorption of nutrients, electrolytes and fluids. Appropriate transit through the esophagus, stomach, small intestine and colon depends on regional control of intraluminal pressure and several sphincters that regulate forward movement and prevent back-flow of gastrointestinal contents. The normal gastrointestinal motility pattern can be impaired by a variety of circumstances including disease and surgery.

Disorders of gastrointestinal motility can include, for example, gastroparesis and gastroesophageal reflux disease (GERD). Gastroparesis is characterized by delayed emptying of stomach contents. Symptoms of gastroparesis include stomach upset, heartburn, nausea and vomiting. Acute gastroparesis can be caused by drugs, viral enteritis and hyperglycemia. The most common underlying disease resulting in gastroparesis is diabetes.

Gastroesophageal reflux is a physical condition in which stomach contents (e.g., stomach acid) reflux or flow back from the stomach into the esophagus. Frequent reflux episodes (e.g., two or more times per week) can result in a more severe problem known as gastroesophageal reflux disease (GERD). The most common symptom of gastroesophageal reflux disease is a burning sensation or discomfort behind the breastbone or sternum and is referred to as dyspepsia or heartburn. Dyspepsia can also mimic the symptoms of myocardial infarction or severe angina pectoris. Other symptoms of gastroesophageal reflux disease disease include dysphagia, odynophagia, hemorrhage, water brash and respiratory manifestations such as asthma, recurrent pneumonia, chronic coughing, intermittent wheezing due to acid aspiration and/or stimulation of the vagus nerve, earache, hoarseness, laryngitis and pharyngitis.

Reflux episodes which result in gastroesophageal reflux disease, can occur both during the daytime (i.e., when the subject is in a waking state) and at nighttime (i.e., when the subject is in a non-waking state). Gastroesophageal reflux disease occurring at nighttime is commonly referred to as nocturnal gastroesophageal reflux disease. Nocturnal gastroesophageal reflux disease is distinct from daytime or diurnal gastroesophageal reflux disease not only in the timing of the reflux episode, but in the severity of the damage which occurs as a result of the reflux. More specifically, nocturnal gastroesophageal reflux disease can be particularly damaging to the pharynx and larynx and a strong association between nocturnal gastroesophageal reflux disease and asthma exists. The increased damage associated with nocturnal gastroesophageal reflux disease is due to a decrease in natural mechanisms which normally help protect against reflux (e.g., saliva production and swallowing), which occur when the patient is sleeping. This decrease leaves the esophagus more vulnerable to damage and can increase microaspiration. In addition, while asleep the body is in the recumbent position, eliminating the effect of gravity, which can clear gastric content from the esophagus. Sleep disorders are also associated with nocturnal gastroesophageal reflux disease resulting in daytime sleepiness and a significant decrease in the overall quality of life.

On a chronic basis, gastroesophageal reflux disease subjects the esophagus to ulcer formation or esophagitis and can result in more severe complications such as, esophageal erosion, esophageal obstruction, significant blood loss and perforation of the esophagus. Severe esophageal ulcerations occur in 20-30% of patients over age 65. In addition to esophageal erosion and ulceration, prolonged exposure of the esophageal mucosa to stomach acid can lead to a condition known as Barrett's Esophagus. Barrett's Esophagus is an esophageal disorder that is characterized by replacement of normal squamous epithelium with abnormal columnar epithelium. This change in tissue structure is clinically important not only as an indication of severe reflux, but as an indication of cancer.

Many factors are believed to contribute to the onset of GERD. A number of factors involve failure of the lower esophageal sphincter mechanism to work properly. The lower esophageal sphincter is tonically contracted to prevent reflux of gastric contents. In a healthy person the muscle relaxes only during swallowing to allow food to pass and also on average three to four times an hour in a phenomenon known as transient lower esophageal sphincter relaxations. In gastroesophageal reflux disease sufferers, the frequency of transient lower esophageal sphincter relaxations can be much higher, for example, as high as eight or more times an hour and weakness of the lower esophageal sphincter allows reflux to occur. Other factors that can contribute to gastroesophageal reflux disease include delayed stomach emptying and ineffective esophageal clearance. Delayed stomach emptying leads to reflux of the gastric contents into the esophagus.

Current methods to treat gastroesophageal reflux disease include lifestyle changes such as weight loss, avoidance of certain foods that exacerbate the symptoms of gastroesophageal reflux disease and avoidance of excessive bending. Elevation of the head of the bed helps reduce nocturnal reflux. While these avoidance strategies can be useful, the efficacy of lifestyle modification alone for the treatment of gastroesophageal reflux disease is not supported.

Medications for the treatment of gastroesophageal reflux disease include conventional antacids, for example, TUMS® and ROLAIDS® which provide only short term relief. $H_2$ receptor antagonists, for example, nizatidine (AXID®), ranitidine (ZANTAC®), famotidine (PEPCID® and PEPCID COMPLETE®), roxatidine (ROTANE® or ZORPEX®) and cimetidine (TAGAMET®), are more effective in controlling gastroesophageal reflux disease, but do not treat the underlying disease. However, patients receiving $H_2$ receptor antagonists develop tolerance to the drugs rendering the drugs ineffective in their ability to inhibit acid secretion.

More powerful secretory inhibitors, such as the proton pump inhibitors, for example, esomeprazole (NEXIUM.RTM.), omeprazole (PRILOSEC.RTM. and RAPINEX.RTM.), lansoprazole (PREVACID.RTM.), rabeprazole (PARIET.RTM., ACIPHEX.RTM.) and pantoprazole (PROTONIX.RTM.) are more effective than the $H_2$ receptor antagonists but are very expensive and their efficacy relies on inhibition of active proton pumps as stimulated by meals, thereby having little or no effect on the occurrence of nocturnal gastroesophageal reflux disease.

Prokinetic drugs are another type of drug used in the treatment of gastrointestinal motility disorders. Prokinetic drugs act to stimulate gastrointestinal motility. Stimulation can occur by direct action on smooth muscle or by an action on the myenteric plexus. The motor functions of the gastrointestinal tract are expressions of a balance at the level of smooth muscle cells between inhibitory mechanisms mainly regulated by dopamine and stimulatory events mainly regulated through the release of acetylcholine. Therefore gastrointestinal motility can be stimulated by dopamine receptor 2 antagonists such as metoclopramide and domperidone, or by substances which release acetylcholine such as metoclopramide or the 5-HT.sub.4 receptor agonist, cisapride (PROPULSID.RTM.), or directly by cholinergic drugs which bind on muscarinic receptors of the smooth muscle cell such as bethanechol. Prokinetic drugs can both stimulate motility and coordinate the activity between different segments of the gastrointestinal tract. However, there are currently no prokinetic drugs available that are both effective and safe. For example, serious cardiac arrhythmias including ventricular tachycardia, ventricular fibrillation, torsades de pointes, and QT prolongation have been reported in patients taking the prokinetic of choice, cisapride. As a result, strict limitations have been imposed on the prescribing of this drug. Further, the use of the dopamine antagonists, metoclopramide and domperidone, is associated with lack of patient tolerability, undesirable CNS effects, such as diskinesia and undesirable cardiovascular effects, such as QT prolongation.

Dopamine (DA) is present in large amounts in the gut and it regulates gastrointestinal (GI) function via inhibition of gastrointestinal motility. This is believed to be due to dopamine-induced suppression of acetylcholine release (a principal excitatory neurotransmitter in the gut) from enteric cholinergic neurons. Although dopamine is an important modulator of enteric function, much remains to be understood about its exact role in the gastrointestinal tract. Traditionally, dopamine has been thought to exert its effects via the D2 receptor (D2R) and hence antagonists of this receptor (metoclopramide and domperidone) are administered to alleviate symptoms associated with various gastrointestinal motility disorders.

The role of newly discovered dopamine receptors such as D3 and D4 in the regulation of gastrointestinal motility is not well known. Due to the side effects associated with current prokinetic drugs in the treatment of disorders related to gastrointestinal motility, it is important to develop newer drugs to manage such disorders. The presence of D3 and D4 dopamine receptors in the GI tract opens up new avenues for treating GI motility disorders that target these receptors.

The instant invention is directed to novel methods of treating GI motility disorders by targeting the dopamine 3 receptors in the GI tract. Prior art is deficient in the lack of useful agents to regulate gastrointestinal motility especially agents that target the dopamine 3 receptor. The present invention fulfills this long-standing need in the art.

SUMMARY OF THE INVENTION

The present invention discloses the role of dopamine D3 receptors (D3R) in the regulation of gastrointestinal motility. In one embodiment, there is provided a method of using an agonist of dopamine 3 receptor or a pharmaceutically acceptable salt thereof to decrease gastrointestinal tract motility or gastric emptying in an animal or human.

In one embodiment the present invention discloses a method for treating gastrointestinal motility disorder caused by at least one condition chosen from inflammatory bowel disease, ulcerative colitis, granulomatous enteritis, infectious diseases of the small or large intestine, pyloric spasm, abdominal cramps, a functional bowel disorder, mild dysenteries, diverticulitis, acute enterocolitis, neurogenic bowel disorders, splenic flexure syndrome, neurogenic colon or spastic colitis by administering an effective dose of a dopamine 3 receptor agonist.

In another embodiment of the present invention, there is provided a method of decreasing gastrointestinal tract motility or gastric emptying in a subject, comprising the step of administering a therapeutically effective amount of PD 128907 hydrochloride or 7-hydroxy-2-dipropylaminotetralin to the subject.

In another embodiment of the present invention, there is provided a method of treating increased gastrointestinal motility in a subject by administering at least one other pharmaceutically active compound besides a dopamine 3 receptor agonist. Some examples of such pharmaceutically active compounds are hexamethonium, trimethaphan, chloroisondamine, erysodine, beta-dihydroerythrodine, amantidine, perpidine, succinylcholine, decamethonium, tubocurarine, atracurium, doxacurium, mivicurium, pancuronium, rocuronium, vencuronium, glycopyrrolate, atropine, hyscomine, scopolamine, loperamide, difenoxine, codeine, morphine, oxymorphone, oxycontin, dihydrocodeine, fentanyl, alosetron hydrochloride, verapamil, amiloride, furosemide, bismuth, sandostatin, sulfasalazine, estrogens, prednisone, prednisolone, cortisol, cortisone, fluticasone, dexamethasone, betamethasone, 5-aminosalicylic acid, metronidazole, ciprofloxacin, azathioprine, 6-mercaptopurine, cyclosporine, methotrexate, fish oil, remicade, heparin, and nicotine.

In another embodiment of the present invention, there is provided a method of using an antagonist of dopamine 3 receptor or a pharmaceutically acceptable salt thereof to increase gastrointestinal tract motility or gastric emptying in an animal or human.

In one embodiment the present invention discloses a method for treating gastrointestinal motility disorder caused by at least one condition chosen from diabetes, infections, endocrine disorders, scleroderma, neuromuscular diseases, cancer, radiation treatment, surgery of the upper intestinal tract, surgery of the stomach, surgery of the esophagus, surgery of the duodenum, anorexia nervosa and bulimia by administering an effective dose of a dopamine 3 receptor antagonist.

In another embodiment of the present invention, there is provided a method of increasing gastrointestinal tract motility or gastric emptying in a subject, comprising the step of administering a therapeutically effective amount of UH232, GR 103691, U-99194A or nafadotride to the subject.

In another embodiment of the present invention, there is provided a method of treating increased gastrointestinal motility in a subject by administering at least one other pharmaceutically active compound besides a dopamine 3 receptor antagonist. Some examples of such pharmaceutically active compounds are esomeprazole, lansoprazole or omeprazole, nizatidine, famotidine, cimetidine, ranitidine, aluminum antacids, calcium antacids, magnesium antacids, metoclopramide, domperidone, fenoldapam mesylate, cabergoline, pramipexole, pergolide mesylate, ropinirole, amanitidine HCL, tegaserod, alosetron, pilocarpine, fluoxetine, paroxetine, erythromycin, and dexloxiglumide.

Other and further aspects, features, and advantages of the present invention will be apparent from the following description of the presently preferred embodiments of the invention. These embodiments are given for the purpose of disclosure.

DETAILED DESCRIPTION OF THE INVENTION

Results presented herein indicate that the dopamine 3 receptor may play an important role in the regulation of gastric motility and contribute to the overall negative effect of dopamine on gastric emptying. An understanding of the role of dopamine and its receptors in the modulation of enteric function will help improve therapeutic strategies for the treatment of several gastrointestinal motility disorders.

Figure 1:
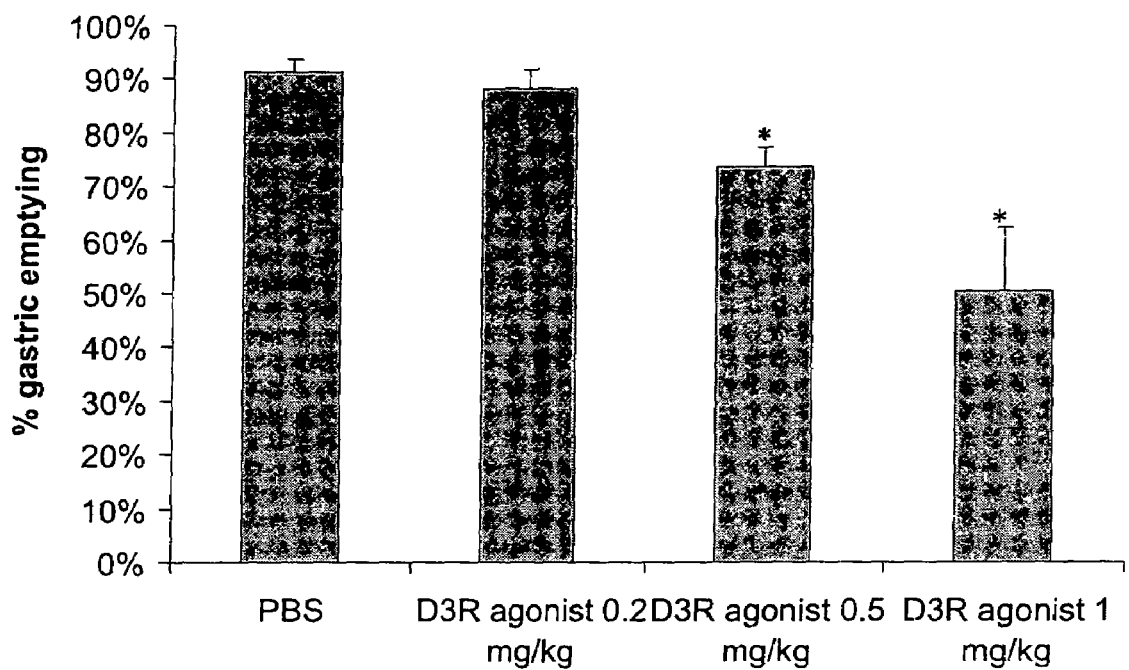
FIG. 1 shows that intraperitoneal injections of dopamine 3 receptor (D3R) agonist significantly delayed gastric emptying in rats (44±8.26% gastric emptying in D3R agonist-treated group versus 78±4.86% in vehicle-treated group, **p<0.01 by Student's t-test).

Intraperitoneal injections of a dopamine 3 receptor (D3R) agonist, PD 128907, significantly delayed gastric emptying in rats (44% gastric emptying in the dopamine 3 receptor agonist-treated group versus 78% in the vehicle-treated group, P<0.01, FIG. 1). This agonist was also shown to reduce the electric field stimulation induced relaxation of pyloric strips of adult male Sprague-Dawley rats when tested in an organ bath. Thus, endogenous dopamine may be acting via the dopamine 3 receptor and antagonism of dopamine 3 receptor may represent an important and novel mechanism to accelerate gastric emptying. Conversely, dopamine 3 receptor agonists may be useful to delay gastric emptying and cause satiety. Hence, modulating dopamine activity through dopamine 3 receptor may be useful in treating patients with gastroparesis, obesity, and gastrointestinal dysmotility.

In one embodiment, there is provided a method of using a therapeutically effective amount of a dopamine 3 receptor agonist or a pharmaceutically acceptable salt thereof to decrease gastrointestinal tract motility or gastric emptying in an animal or human. Preferably, the method is useful for treating a human suffering from nausea, vomiting and obesity.

In one embodiment, a dopamine 3 receptor agonist may be used to treat increased gastrointestinal motility caused by at least one condition selected from the group comprising of inflammatory bowel disease, ulcerative colitis, granulomatous enteritis, infectious diseases of the small or large intestine, pyloric spasm, abdominal cramps, a functional bowel disorder, mild dysenteries, diverticulitis, acute enterocolitis, neurogenic bowel disorders, splenic flexure syndrome, neurogenic colon and spastic colitis.

The invention also discloses the use of dopamine 3 receptor agonists to treat an increase in gastrointestinal motility caused by medications. Representative examples of useful dopamine 3 receptor agonists include PD 128907 hydrochloride or 7-hydroxy-2-dipropylaminotetralin (7-OH-DPAT).

The present invention further discloses that a dopamine 3 receptor agonist may be administered in combination with at least one other pharmaceutically active compound to treat a gastrointestinal motility disorder. Examples of such pharmaceutically active compounds include hexamethonium, trimethaphan, chloroisondamine, erysodine, beta-dihydroerythrodine, amantidine, perpidine, succinylcholine, decamethonium, tubocurarine, atracurium, doxacurium, mivicurium, pancuronium, rocuronium, vencuronium, glycopyrrolate, atropine, hyscomine, scopolamine, loperamide, difenoxine, codeine, morphine, oxymorphone, oxycontin, dihydrocodeine, fentanyl, alosetron hydrochloride, verapamil, amiloride, furosemide, bismuth, sandostatin, sulfasalazine, estrogens, prednisone, prednisolone, cortisol, cortisone, fluticasone, dexamethasone, betamethasone, 5-aminosalicylic acid, metronidazole, ciprofloxacin, azathioprine, 6-mercaptopurine, cyclosporine, methotrexate, fish oil, remicade, heparin, and nicotine.

Figure 3:
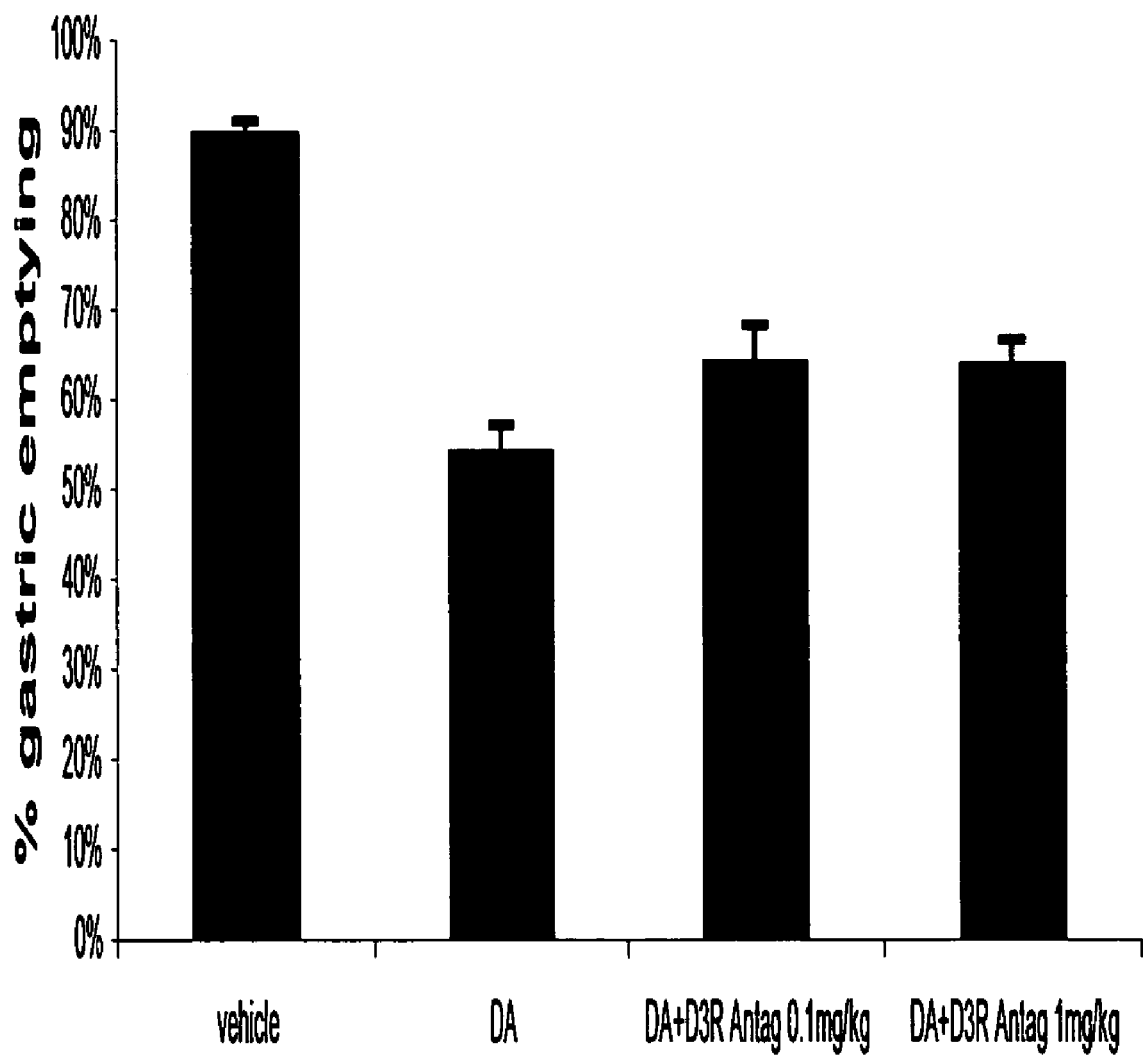
FIG. 3 shows the partial reversal of the effect of dopamine on gastric emptying by the dopamine 3 receptor (D3R) antagonist, nafadotride. Gastric emptying was assessed in adult male Sprague-Dawley rats by the phenol red method. Twenty minutes after feeding a non-nutrient methylcellulose meal to rats treated with dopamine (DA, 1 mg/kg i.p.) or with dopamine plus varying doses of nafadotride (D3R Antag, 0.1 or 1 mg/kg i.p.). Control rats received vehicle (PBS).

In another embodiment, there is provided a method of using a therapeutically effective amount of a dopamine 3 receptor antagonist or a pharmaceutically acceptable salt thereof to increase gastrointestinal tract motility or gastric emptying in an animal or human. Preferably, the method is useful for treating gastroparesis from any cause including but not limited to diabetic gastroparesis, gastroesophageal reflux disease, anorexia, bulimia, scleroderma, neuromuscular diseases and endocrine disorders. FIG. 3 illustrates the partial reversal of the effect of dopamine on gastric emptying by the dopamine 3 receptor antagonist, nafadotride. This demonstrates that dopamine 3 receptor antagonists can effectively increase gastrointestinal tract motility or gastric emptying in an animal or human.

In one embodiment, the invention discloses the use of dopamine 3 receptor antagonist to treat a decrease in gastrointestinal motility caused by medications such as narcotic pain medications, calcium channel blockers and antidepressants.

In one embodiment, a dopamine 3 receptor antagonist may be used to treat a decrease in gastrointestinal motility caused by at least one condition selected from the group comprising of diabetes, infections, endocrine disorders, scleroderma, neuromuscular diseases, cancer, radiation treatment, surgery of the upper intestinal tract, surgery of the stomach, surgery of the esophagus, surgery of the duodenum, anorexia nervosa and bulimia.

Representative examples of useful dopamine 3 receptor antagonists include GR 103691, UH232, U-99194A and nafadotride.

The present invention further discloses that a dopamine 3 receptor antagonist may be administered in combination with at least one other pharmaceutically active compound to treat a gastrointestinal motility disorder. Examples of such pharmaceutically active compounds include esomeprazole, lansoprazole or omeprazole, nizatidine, famotidine, cimetidine, ranitidine, aluminum antacids, calcium antacids, magnesium antacids, metoclopramide, domperidone, fenoldapam mesylate, cabergoline, pramipexole, pergolide mesylate, ropinirole, amanitidine HCL, tegaserod, alosetron, pilocarpine, fluoxetine, paroxetine, erythromycin, and dexloxiglumide.

A "therapeutically effective amount" as used in the instant invention refers to an amount effective, at dosages and for periods of time necessary, to achieve the desired therapeutic result, such as decreasing or increasing gastrointestinal tract motility or gastric emptying. A therapeutically effective amount of dopamine 3 receptor agonist or antagonist may vary according to factors such as the disease state, age, sex, and weight of the individual. A therapeutically effective amount is also one in which any toxic or detrimental effects are outweighed by the therapeutically beneficial effects. One of ordinary skill in the art would readily adjust dosage regimens to provide optimum therapeutic response without undue experimentation.

When the dopamine 3 receptor agonist or antagonist is administered in combination with at least one other pharmaceutically active compound, the other active pharmaceutical compound may be used, for example, in those amounts indicated in the PDR or as otherwise determined by one of ordinary skill in the art.

The dopamine receptor 3 antagonist or agonist can be administered for any of the uses described herein by any suitable means, for example, orally, such as in the form of tablets, capsules, granules or powders; sublingually; bucally; parenterally, such as by subcutaneous, intravenous, intramuscular, or intrasternal injection or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories; in dosage unit formulations containing non-toxic, pharmaceutically acceptable vehicles or diluents. The present compounds can, for example, be administered in a form suitable for immediate release or extended release. Immediate release or extended release can be achieved by the use of suitable pharmaceutical compositions comprising the present compounds, or, particularly in the case of extended release, by the use of devices such as subcutaneous implants or osmotic pumps. The present compounds can also be administered liposomally.

Representative examples of oral administration include suspensions which can contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which can contain, for example, microcrystalline cellulose, dicalcium phosphate, starch, magnesium stearate and/or lactose and/or other excipients, binders, extenders, disintegrants, diluents and lubricants such as those known in the art. The dopamine 3 receptor agonist or antagonist can also be delivered through the oral cavity by sublingual and/or buccal administration. Molded tablets, compressed tablets or freeze-dried tablets are exemplary forms which may be used. Exemplary compositions include formulations with fast dissolving diluents such as mannitol, lactose, sucrose and/or cyclodextrins. Also included in such formulations may be high molecular weight excipients such as celluloses (avicel) or polyethylene glycols (PEG). Such formulations can also include an excipient to aid mucosal adhesion such as hydroxypropyl cellulose (HPC), hydroxypropyl methyl cellulose (HPMC), sodium carboxymethyl cellulose (SCMC), maleic anhydride copolymer (e.g., Gantrez), and agents to control release such as polyacrylic copolymer (e.g. Carbopol 934). Lubricants, glidants, flavors, coloring agents and stabilizers may also be added for ease of fabrication and use.

Exemplary compositions for nasal, aerosol, or inhalation administration include solutions in saline which can contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which can contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid, or Cremaphor.

Exemplary compositions for rectal administration include suppositories which can contain, for example, a suitable non-irritating excipient, such as cocoa butter, synthetic glyceride esters or polyethylene glycols, which are solid at ordinary temperatures, but liquefy and/or dissolve in the rectal cavity to release the drug.

Exemplary compositions for topical administration include a topical carrier such as Plastibase (mineral oil gelled with polyethylene).

The effective amount of a dopamine 3 receptor agonist or antagonist to treat a gastrointestinal motility disorder can be determined by one of ordinary skill in the art, and includes exemplary dosage amounts for a adult human of from about 0.001 to 100 mg/kg of body weight of active compound per day, preferably 0.01 to 1 mg/kg of body weight of active compound per day, that can be administered in a single dose or in the form of individual divided doses, such as from 1 to 4 times per day. It is well understood that the specific dose level and frequency of dosage for any particular subject can be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like, subject to motility-associated conditions.

The following examples are given for the purpose of illustrating various embodiments of the invention and are not meant to limit the present invention in any fashion. The present examples, along with the methods, procedures, treatments, molecules, and specific compounds described herein are presently representative of preferred embodiments. One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

EXAMPLE 1

Gastric Emptying Test

A solution of 50 mg phenol red in 100 ml aqueous methylcellulose (1.5%) was used as a test meal. Methylcellulose (1.5 g, 400 centipoises) was dispersed in 100 ml of hot water (80° C.) under continuous shaking. The solution was allowed to cool to 35° C., and then phenol red was added. Intensity and duration (5 hr) of agitation were kept constant to obtain solutions of reproducible viscosity.

Conscious rats were fed the 0.05% phenol red methylcellulose solution and euthanized after 20 minutes. The stomach was clamped at the pylorus and cardiac ends before removal. The stomach and its contents were homogenized with 100 ml of 0.1N NaOH. A baseline control for each phenol red solution preparation was used by mixing 1.5 ml with 100 ml of 0.1N NaOH. The mixture was then kept for 1 hr at room temperature: 5 ml of the supernatant was added to 0.5 ml of trichloroacetic acid solution (20% w/v) to precipitate the proteins. After centrifugation (2500×g for 20 min) the supernatant was added to 4 ml of NaOH (0.5 N) to develop maximum intensity of the color. The solutions were then read with a spectrophotometer at a wavelength of 560 nm.

Gastric emptying (G.E.) for each rat was calculated according to the following formula: (1−Absorbance of test sample)/(Absorbance of baseline control)×100%. Values were expressed as mean±SEM. Two-tailed Student's t-test was used for comparison between groups.

EXAMPLE 2

Effect of Dopamine 3 Receptor Agonist on Gastric Emptying

Adult male Sprague-Dawley rats (weighing 200-250 g) were deprived of food 18 hr prior to experiments but allowed free access to water. The animals were intraperitoneally injected with a dopamine 3 receptor agonist, PD 128907 hydrochloride, at 1 mg/kg or with physiological saline (control) before administration by oral tube of 1.5 ml of prewarmed (35° C.) 0.05% phenol red solution.

As shown in FIG. 1, systemic activation of dopamine 3 receptor (D3R) significantly delays gastric emptying in the rat, suggesting D3R plays an important role in the regulation of gastric motility.

EXAMPLE 3

Effect of Dopamine 3 Receptor Agonist on Pyloric Function

Figure 2:
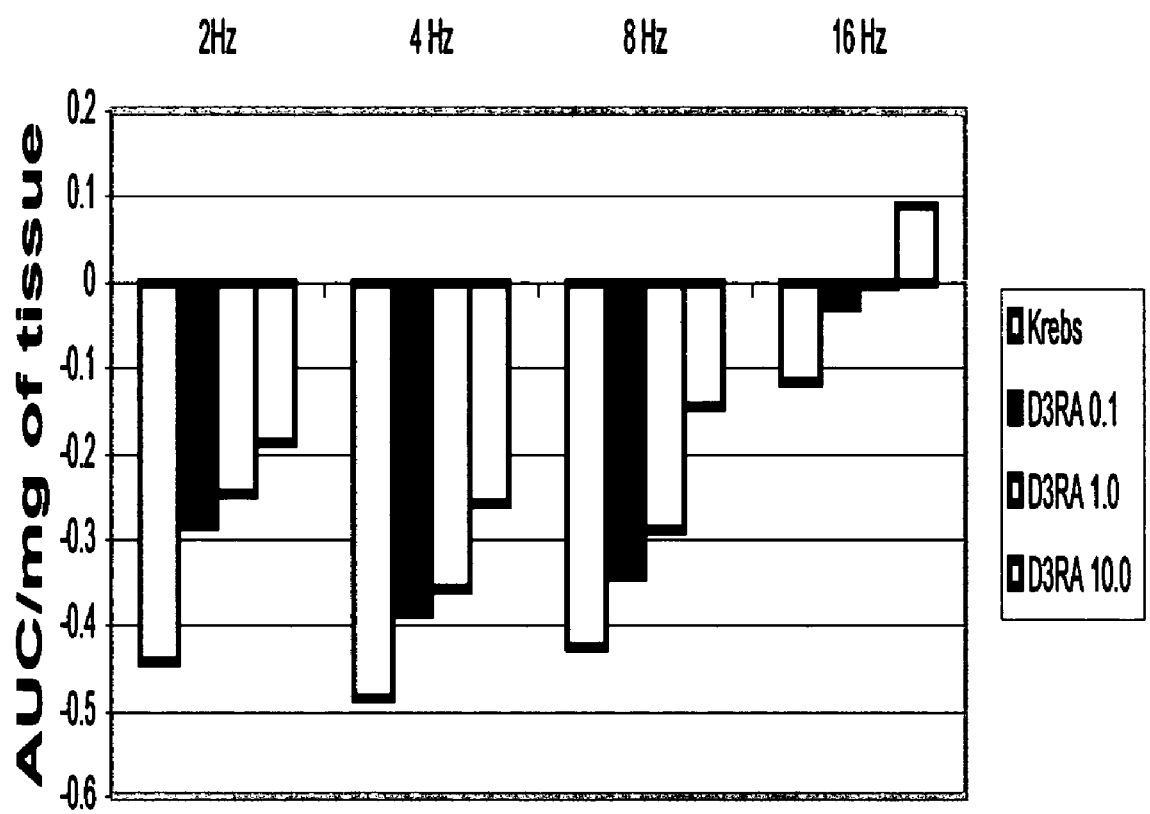
FIG. 2 shows the reduced electric field stimulation induced relaxation of pyloric strips derived from adult male Sprague-Dawley rats in an organ bath in the presence of the D3R agonist, PD 128907 hydrochloride (D3RA, P=0.011 by two-way ANOVA). The pyloric function was assessed by measuring the relaxation of pyloric strips in an organ bath in response to electric field stimulation in the presence of D3R agonist ranging from 0.1-10 $\square$M (1 $\square$M vs control, P<0.05; 10 µM vs control, P=0.001).

Pyloric function was assessed in an organ bath by measuring the relaxation of pyloric strips of adult male Sprague-Dawley rats in the presence of the dopamine 3 receptor agonist, PD 128907 hydrochloride. FIG. 2 illustrates the significant reduction in electric field stimulation induced relaxation of pyloric strips in the presence of the agonist. The figure clearly shows that this effect was dose dependent, showing a greater decrease in relaxation with increasing doses of the D3R agonist.

EXAMPLE 4

Effect of Dopamine 3 Receptor Antagonist on Gastric Emptying

Adult male Sprague-Dawley rats were used in the study. Gastric emptying was assessed by the phenol red method 20 minutes after feeding a non-nutrient methylcellulose meal to rats treated intraperitoneally with dopamine or dopamine plus varying doses of a selective dopamine 3 receptor antagonist, nafadotride (0.1 or 1 mg/kg body weight). Control rats were given an intraperitoneal injection of the vehicle, phosphate buffered saline.

Nafadotride was able to partially reverse the effect of dopamine on the gastric emptying time as illustrated in FIG. 3.

What is claimed is:

1. A method of increasing gastric emptying in a subject, suffering from gastroesophageal reflux due to a decrease in gastrointestinal motility, comprising the step of administering a therapeutically effective amount of nafadotride or a pharmaceutically acceptable salt thereof to the subject.

2. The method of claim 1, wherein the subject is an animal or a human.

3. The method of claim 1, wherein the nafadotride is present in a pharmaceutically acceptable sustained release formulation.

4. The method of claim 1, wherein the nafadotride is administered via oral, nasal, intradermal, parenteral, mucosal, buccal, rectal or topical route.

* * * * *